United States Patent [19]

Gervasutti

[11] Patent Number: 5,059,729

[45] Date of Patent: Oct. 22, 1991

[54] PROCESS FOR PREPARING 1,2-DIFLUOROETHANE AND 1,1,2-TRIFLUOROETHANE

[75] Inventor: Claudio Gervasutti, Mestre, Italy

[73] Assignee: Ausimont S.r.l., Milan, Italy

[21] Appl. No.: 680,620

[22] Filed: Apr. 2, 1991

Related U.S. Application Data

[63] Continuation of Ser. No. 545,762, Jun. 29, 1990, abandoned, which is a continuation of Ser. No. 464,653, Jan. 11, 1990, abandoned, which is a continuation of Ser. No. 296,068, Jan. 12, 1989, abandoned.

[30] Foreign Application Priority Data

Jan. 15, 1988 [IT] Italy .............................. 19077 A/88

[51] Int. Cl.$^5$ .............................................. C07C 17/00
[52] U.S. Cl. ...................................... 570/175; 570/176
[58] Field of Search .................................. 570/175, 176

[56] References Cited

FOREIGN PATENT DOCUMENTS 593529 3/1960 Canada ................................. 570/176
3619079 12/1986 Fed. Rep. of Germany ...... 570/176

*Primary Examiner*—Alan Siegel
*Attorney, Agent, or Firm*—Morgan & Finnegan

[57] ABSTRACT

A process for preparing 1,2-difluoroethane or 1,1,2-trifluoroethane by hydrogenation of 1,2-dichlorodifluoroethylene or 1-chlorotrifluoroethylene in the presence of a hydrogenation catalyst. The process is conducted in the gas phase at a temperature ranging from 100° C. to 220° C., the molar ratios between $H_2$ and olefin being higher than 3.

4 Claims, No Drawings

PROCESS FOR PREPARING 1,2-DIFLUOROETHANE AND 1,1,2-TRIFLUOROETHANE

This is a continuation of co-pending application Ser. No. 545,762, filed on June 29, 1990 now abandoned which is a continuation of Ser. No. 464,653, filed Jan. 11, 1990, now abandoned, which is a continuation of Ser. No. 296,068, filed Jan. 12, 1989, now abandoned.

BACKGROUND OF THE INVENTION

This invention relates to a process for preparing partially hydrogenated fluorinated hydrocarbons, in particular it relates to the preparation of 1,2-difluoroethane and of 1,1,2-trifluoroethane by catalytic hydrogenation of 1,2-dichlorodifluoroethylene and 1-chlorotrifluoroethylene, respectively.

1,2-difluoroethane $CH_2F$—$CH_2F$ is a well-known fluorinated hydrocarbon which is utilizable, in admixture with other hydrocarbons, as a fluid for the Rankine cycle, as a cooling medium (U.S. Pat. No. 4,055,049) or as a starting material for the preparation of fully substituted brominated derivatives.

1,2-difluoroethane and 1,1,2-trifluoroethane can be used also as components of propellant mixtures for aerosols.

In fact, although the assumption that a possible accumulation of fluorinated hydrocarbons may lead to a degradation of the stratospheric ozone is still to be proved, conversely it seems probable that the hydrogen-containing fluorocarbons do not raise any problems in this respect.

The prior art does not describe any specific method of preparing 1,2-difluoroethane which can be easily practiced on an industrial scale, or which is capable of providing this product with a high yield and a high selectivity. Conversely, the prior art describes general methods for the treatment of variously substituted ethane, from which it is possible to obtain a mixture of products in which also 1,2-difluoroethane may be present as a by-product.

These general methods include the direct fluorination of $CH_3$—$CH_2F$ with $F_2$ (Cadmau P., Kirk A. W.; Trotman—Dickenson A. F. J. Chem. Soc., Faraday Trans. 1), the electrochemical fluorination of ethane at 100° C. (Fox H. M., Ruehlen F. N. Childs, W. V.; J. Electochem. Soc. 1971, 118(7), 1246–9) and the fluorination of ethane with potassium tetrafluorocolbaltate ($KCoF_4$) and $CoF_3$ (Burdon J.; Knights J.; Parson I.; Tatlow J. - Tetrahedron 1976, 32(9), 1041–3).

All the above-described processes are very difficult to practice on an industrial scale either due to the high costs of the equipment involved by the presence of $F_2$, or due to the use of catalysts such as, for example, $CoF_3$, which requires particularly sophisticated apparatus for the regeneration with $F_2$, which is necessary due to the catalyst reduction during the reaction.

French patent application No. 86,08389 in the name of the Applicant hereof describes a process for preparing halogenated olefins by catalytic hydrogenation of 1,2-dichlorodifluoroethylene at temperatures higher than 100° C., in particular from 200° to 600° C., preferably from 300° C. to 400° C.

According to the teaching of said patent application, the hydrogenolysis of 1,2-dichlorodifluoroethylene in the presence of palladium as a catalyst involves the partial or total substitution of chlorine, while the ethylenic unsaturation of the starting compound is left unaltered. All the experimental examples described in the cited French patent application were operated at a temperature of 300° C. or 350° C.

High conversions, even higher than 90%, were obtained and, as by-products, a mixture of $CH_2F$—$CH_2F$, $CHClF$—$CHClF$ and $CH_2$=$CHF$, in an amount not exceeding 20%, was obtained.

According to this patent application, the molar ratio between hydrogen and olefin can vary over a wide range, from 0.5 to 10, preferably from 3 to 5. The lower the reaction temperature the greater is the necessity to use high ratios between hydrogen and olefins, namely higher than a ratio of 2:1, in order to obtain high yields of the olefins. The temperature being equal, high yields of the olefins are obtained if it is operated with high molar ratios, higher than 2:1.

From an older patent application filed by the Applicant (European patent application 253,410) it is known how to prepare fluorinated or chloroinated olefins, in particular fluoro- and chloroethylenes such as $CHF$=$CHF$ and $CFCl$=$CFH$, starting from chlorofluoroethanes and hydrogen in the presence of hydrogenation catalysts.

The reaction temperatures range from 150° to 600° C., preferably from 200° to 400° C.

According to the process of said application, experimental tests have proved that it is necessary to operate at high temperatures and with high ratios between hydrogen and chlorofluoroethane in order to obtain high conversions.

However, tho conversion is never total, its maximum value being about 85%, which leads, in the course of time, to a deactivation of the catalyst and, by consequence, to serious drawbacks for a commercial-scale process.

OBJECTS OF THE INVENTION

Thus, an object of the present invention is to provide a process for preparing 1,2-difluoroethane with high yields and high conversions, free from the above-cited drawbacks, among which in particular, the deactivation of the catalyst in the long run.

A further object of the invention is to provide a process for selectively preparing 1,1,2-trifluoroethane, which comprises reacting 1-chlorotrifluoroethylene (CTFE) with hydrogen in the presence of a hydrogenation catalyst. The process is carried out in the gas phase at temperatures ranging from 100° C. to 220° C.

The applicant has surprisingly found that if a particular combination of specific operative parameters is used, it is possible to obtain, with high yields and high conversions, 1,2-difluoroethane and 1,1,2-trifluoroethane.

The reaction temperature is the most critical parameter for the process of the present invention, in combination with other parameters such as the contact time between $H_2$ and olefin and the $H_2$: reagents molar ratio, in order to obtain a high conversion of the reagents and high yields of products.

It has been surprisingly found that if the hydrogenolysis is conducted at temperatures ranging from 100° to 220° C., with contact times higher than 30 seconds and $H_2$: reagents molar ratios ranging from 3 to 10, the starting compounds lose the ethylenic unsaturation and 1,2-difluoroethane and 1,1,2-trifluoroethane are obtained with high yields and conversions, and the catalyst can be used for very long times without exhibiting deactivation.

Preferably, the parameter combination is as follows: a temperature from 120° to 180° C., a contact time from 30 to 45 seconds and molar ratios between hydrogen and starting olefin from 4 to 6 for 1,2-dichlorodifluoroethylene and from 3.5 to 5 for 1-chlorotrifluoroethylene.

At temperatures higher than 220° C., the yield of 1,2-difluoroethane and of 1,1,2-trifluoroethane drastically decreases, while at temperatures lower than 100° C. the conversion of 1,2-dichlorodifluoroethylene and of 1-chlorotrifluoroethylene is rather low and of no interest from an industrial viewpoint.

1,2-dichlorodifluoroethylene and CTFE utilized as a starting product in the process of the present invention are commercial products, easily preparable by dechlorination of 1,2-difluorotetrachloroethane and of $CCl_2F-CClF_2$.

According to the process of the present invention, a gaseous mixture of hydrogen and olefin in a molar ratio ranging from 3:1 to 10:1 is caused to flow through the reaction area in order to bring the mixture into intimate contact with the catalyst, maintained at 100°–220° C. for 30–60 seconds, with the products recovered from the effluent gases.

The catalytic hydrogenation process of the invention can be conducted both at atmospheric pressure and at a higher pressure; pressure values up to 15 bar can be used.

One of the most important factors of the process of the present invention is, as already pointed out, the reaction temperature. This parameter, however, must be evaluated as a function of the contact times and of the ratios between the reagents.

In order to obtain high conversions and high yields it is preferable to maintain the contact time between 30 and 60 seconds. In fact, contact times lower than 30 seconds result in a strong decrease in the conversion of the starting compounds, while contact times higher than 1 minute are useless and do not lead to a substantial increase in the conversion and yield.

The hydrogen olefin molar ratio shall range from 3 to 10 and preferably from 4 to 6 for 1,2-dichlorodifluoroethylene and from 3.5 to 5 for 1-chlorotrifluoroethylene. In fact, when the molar ratios are lower than 3, a drastic reduction in the conversion of the starting product occurs, while if hydrogen is utilized in high amounts, the unreacted hydrogen in excess cannot be recovered unless complex procedures are used.

The catalytic bed on which the reagent gaseous mixture is made to flow consists of a hydrogenation catalyst, which may consist of a transition metal such as palladium, platinum, nickel, chrome, copper, either as such or, preferably, supported on an inert material such as, for example, carbon, alumina, $BaSO_4$, etc., at concentrations from 0.1 to 5% by weight.

Preferably, the catalyst consists of palladium, optionally supported on carbon, at concentrations ranging from 0.1 to 5% by weight. Small amounts, up to 10%, by weight, of other metal catalysts (for example copper, nickel, chrome) can be added to the basic catalyst metal.

Hydrogen can be fed either in the pure state or diluted with an inert gas such as e.g. nitrogen, helium, argon, etc.

Hydrogenation is usually conducted in tubular reactors made of materials which are inert toward the reagents, the products and the by-products of the reaction, such as nickel, Inconel, stainless steel etc.

The reaction products and the unconverted reagents can be recovered and isolated by conventional methods. For example, the gases flowing out from the reactor are made to pass first through an aqueous solution containing alkaline hydroxide in order to remove the hydrochloric acid, then they are anhydrified on $CaSO_4$ and, at last, condensed in a trap cooled with dry ice and methanol.

The following illustrative examples are given to facilitate the understanding of the present invention; however, they are not to be considered as limiting in any manner the scope of the invention.

In the examples, parts and percentages, unless otherwise specified, are by weight.

EXAMPLE 1

Into a cylindrical reactor made of AISI 316, having an inside diameter of 5.4 cm and a length of 70 cm, containing 480 cm$^3$ of activated carbon granules with a palladium content of 1% by weight, thermoregulated at 130° C., were introduced, at atmospheric pressure, 1.28 moles/hour of a mixture, preheated to 90° C., of hydrogen and of 1,2-dichlorodifluoroethylene in a $H_2:C_2Cl_2F_2$ molar ratio of 5:1. The contact time was of 40 seconds.

The vapors leaving the reactor were washed with a NaOH solution at 5% in order to remove hydrochloric acid, anhydrified with calcium sulphate and condensed in a trap cooled to $-70°$ C. with dry ice and methanol.

After washing with the NaOH solution, the vapors leaving the reactor exhibited, on gas-chromatographic analysis, the following composition:

| | |
|---|---|
| 1,2-difluoroethane ($CH_2F-CH_2F$) | 90% |
| 1,2-difluoroethylene ($CHF=CHF$) | 5% |
| 1-chloro-2-fluoroethane ($CH_2Cl-CH_2F$) | 3% |
| unreacted 1,2-dichloro-difluoroethylene ($CClF=CClF$) | absent. |

The balance to 100% consisted of by-products such as $CHF=CClF$, $CH_2=CHF$.

EXAMPLE 2

Into the reactor described in example 1, thermoregulated at 200° C., a hydrogen: 1,2-dichlorodifluoroethylene mixture in a molar ratio of 4:1 was introduced. The contact time was of 35 seconds. The catalyst used and the other modalities are the same as in Example 1.

The vapors, after having left the reactor and after an alkaline washing, were subjected to gas-chromatographic analysis; the weight percentages obtained were as follows:

| | |
|---|---|
| 1,2-difluoroethane | 60% |
| 1,2-difluoroethylene | 20% |
| 1-chloro-1,2-difluoroethylene | 7% |
| 1-chloro-2-fluoroethane | 8% |

EXAMPLE 3

To a cylindrical nickel reactor having an internal diameter of 2 cm and a useful volume of 160 cm$^3$, thermoregulated at 150° C. and containing 100 ml of activated carbon granules with a palladium content of 0.5%, were fed 0.22 moles/h of a mixture of hydrogen:1,2-dichloro-difluoroethylene in a molar ratio of 5:1.

The gas-chromatographic analysis of the vapors leaving the reactor, after the aqueous washing, gave the following results:

| | |
|---|---|
| 1,2-difluoroethane | 75% |
| 1,2-difluoroethylene | 12% |
| 1-chloro-1,2-difluoroethylene | 7% |
| 1-chloro-2-fluoroethane | 3% |

EXAMPLE 4

Comparative Example with Example 3

To a cylindrical nickel reactor, thermoregulated at 150° C., having an inside diameter of 2 cm and a useful volume of 160 cm$^3$ containing 100 cm$^3$ of activated carbon granules with a palladium content of 1% by weight, a hydrogen: 1,2-dichloro-difluoroethylene mixture with a molar ratio of 4:1 was fed at a flow rate of 0.66 moles/h. The contact time was 15 seconds.

The gas-chromatographic analysis of the vapors flowing out from the reactor, carried out after an aqueous washing, gave the following results:

| | |
|---|---|
| 1,2-difluoroethane | 3% |
| 1,2-difluoroethylene | 6% |
| 1-chloro-1,2-difluoroethylene | 20% |
| unreacted 1,2-dichlorodifluoroethylene | 70% |

EXAMPLE 5

Comparative Example with Example 3

Operating under the conditions of example 4, to the same catalytic system, thermoregulated at 150° C., were fed 0.22 moles/h of a mixture of hydrogen and 1,2-dichlorodifluoroethylene in a H$_2$:C$_2$Cl$_2$F$_2$ molar ratio of 2:1.

The organic vapors leaving the reactor were subjected, after an alkaline washing, to gas-chromatographic analysis and gave the weight percentages indicated hereinbelow. The contact time was 45 seconds.

| | |
|---|---|
| 1,2-difluoroethane | 2% |
| 1,2-difluoroethylene | 8% |
| 1-chloro-1,2-difluoroethylene | 15% |
| unreacted 1,2-dichlorodifluoroethylene | 75% |

EXAMPLE 6

In a cylindrical reactor made of AISI 316 and having an internal diameter of 5 cm. and a length of 50 cm., which contains 230 cm$^3$ of active carbon with a contents in palladium of 1% by weight and which is thermoregulated at 130° C., there are added, at atmospheric pressure, 0.83 moles/h of a mixture, preheated at 70° C., of H$_2$ and 1-chlorotrifluoroethylene in a molar ratio H$_2$:C$_2$ClF$_3$ of 3.75:1. The contact time amounted to 30 seconds.

The vapors leaving the reactor, after an alkaline washing, gave by gaschromatographic analysis, the following composition, expressed in percent by weight:

| | |
|---|---|
| 1,1,2-trifluoroethane | 96% |
| trifluoroethylene | 1% |
| unreacted 1-chlorotrifluoroethylene | 2% |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A process for preparing 1,2-difluoroethane, which comprises reacting 1,2-dichlorodifluoroethylene with hydrogen in the gas phase at a temperature in the range of from 100° C. to 220° C. for a contact time ranging from 30 to 60 seconds, the molar ratio between H$_2$ and olefin being from 4 to 6, in the presence of a hydrogenation catalyst of palladium supported on carbon at concentrations of 0.1 to 5% by weight.

2. The process of claim 1, wherein the temperature ranges from 120° to 180° C.

3. The process of claim 1, wherein the contact time of the reagent mixture on the catalytic bed ranges from 30 to 45 seconds.

4. The process of claim 1, wherein the H$_2$/1,2-dichlorodifluoroethylene molar ratio is in the range of 4:1 to 6:1.

* * * * *